United States Patent [19]

Wendzel

[11] Plant 4,055

[45] May 17, 1977

[54] REDKIST

[75] Inventor: Alton C. Wendzel, Watervliet, Mich.

[73] Assignee: Hilltop Orchards & Nurseries, Inc., Hartford, Mich.

[21] Appl. No.: 647,004

[22] Filed: Jan. 7, 1976

[51] Int. Cl.[2] ..... A01H 5/03

[52] U.S. Cl. ..... Plt./43

[58] Field of Search ..... Plt./43

*Primary Examiner*—Robert E. Bagwill
*Attorney, Agent, or Firm*—John R. Nesbitt

EXEMPLARY CLAIM

1. A new and distinct variety of peach tree substantially as shown and described.

1 Drawing Figure

1

This invention is a new and distinct variety of peach tree discovered by Alton C. Wendzel as a limb mutation on a Redskin variety peach tree. It originated in a cultivated area in an orchard owned by Alton C. Wendzel on real estate described as the West Half of the Southeast Quarter of the Northeast Quarter and the East Half of the Southwest Quarter of the Northeast Quarter, all in Section 11, Township 4 South, Range 12 West, Watervliet Township, Berrien County, Mich.

The mutated limb was propagated by bud grafting into young trees near the original tree and at several other locations starting about 1967. The unique characteristics of the sported limb have been maintained through asexual propagation.

The fruit, a branch, and typical leaves are depicted in the enlarged color photograph that is part of this application. The following description is based on fruit from both the original and asexually propagated trees.

TREE

Form: The tree is vigorous and upright spreading, and closely resembles the parent variety Redskin.

LEAF

Color: Same as Redskin.

Shape: Very long and ovate, slightly narrower than Redskin.

Leaf Glands: Kidney shaped and deeply dished.

Leaf Blades: Medium to dark green, the upper surface is smooth and somewhat duller than Redskin, and the lower surface is smooth and dull with the leaf veins slightly raised.

Leaf Margin: Serrations are irregular but prominent and very distinct. The tips are pointed, but duller than Redskin. Margins are fairly straight with less waving than Redskin.

Size: About 5 to 7 inches in length, and about 1¼ to 1½ inches in width.

2

Petiole: Length about ⅜ inch to ½ inch, with color of generally light green at the leaf blade generally shading to a reddish-purple at the abcision point.

FLOWER

Large for a peach, showy, light pink on the outer ends and darkening to bright pink at the center of the blossom. The flower bud is more tolerant of dormant season low temperatures than Redskin.

FRUIT

Substantially round and when compared with Redskin variety, the fruit is distinctively more round, having a high shoulder on the suture side and a more recessed distal end.

Color: When compared with Redskin, the fruit has a brighter yellow groundcolor, and a brighter red overcolor.

Skin: Very smooth, with light pubescence, suture line quite smooth.

Fruit and Pit Size: The fruit averages 2½ inches, and is very uniform. The pits are small compared to similar sized peaches, being about ⅝ inch thick and ⅞ inch wide by 1⅛ inches long. The pit size is characteristic of the Redskin parent which also has a relatively small pit when compared to most other peaches.

Flesh: Clear yellow, smooth, melting, with some red at the pit cavity. The flesh is non-oxydizing.

Quality: Excellent, mild sub acid flavor.

Aroma: Very pleasant.

Maturity: Maturity is 7–10 days earlier than Redskin.

Keeping Quality: Good, equal to Redskin, both for shipping and holding.

Use: Excellent for dessert use, flesh is non-browning, well adapted for both commercial canning and freezer preservation.

1. A new and distinct variety of peach tree substantially as shown and described.

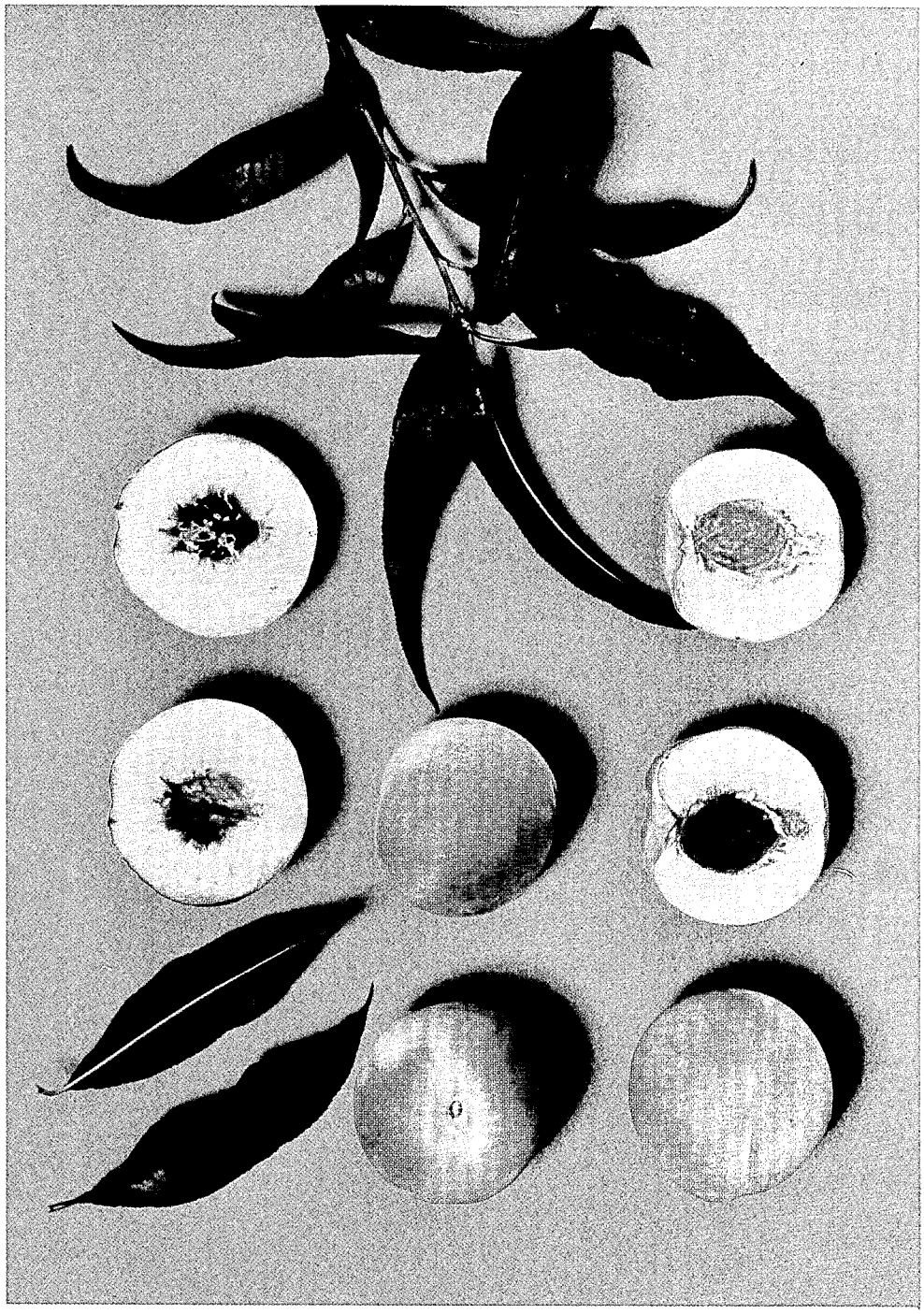

* * * * *